United States Patent
Ludwig et al.

(10) Patent No.: US 12,076,554 B2
(45) Date of Patent: Sep. 3, 2024

(54) PENETRATION OF CEREBRAL SPINAL FLUID INTO THE BRAIN PARENCHYMA USING TEMPORALLY PATTERNED NEUROMODULATION

(71) Applicant: Wisconsin Alumni Research Foundation, Madison, WI (US)

(72) Inventors: Kip Ludwig, Middleton, WI (US); Justin Williams, Cambridge, WI (US); Angela Williams, Cambridge, WI (US); Samuel Poore, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 93 days.

(21) Appl. No.: 17/854,078

(22) Filed: Jun. 30, 2022

(65) Prior Publication Data

US 2022/0331583 A1 Oct. 20, 2022

Related U.S. Application Data

(63) Continuation of application No. 16/935,386, filed on Jul. 22, 2020, now Pat. No. 11,395,914.

(60) Provisional application No. 62/884,002, filed on Aug. 7, 2019.

(51) Int. Cl.
*A61N 1/05* (2006.01)
*A61N 1/04* (2006.01)
*A61N 1/36* (2006.01)

(52) U.S. Cl.
CPC ......... *A61N 1/0548* (2013.01); *A61N 1/0432* (2013.01); *A61N 1/36025* (2013.01)

(58) Field of Classification Search
CPC ............... A61N 1/0548; A61N 1/0432; A61N 1/36025; A61N 1/0526; A61N 2005/0606
See application file for complete search history.

(56) References Cited

U.S. PATENT DOCUMENTS

| | | | |
|---|---|---|---|
| 2005/0159790 A1* | 7/2005 | Shalev | A61M 5/1723 607/45 |
| 2017/0224990 A1* | 8/2017 | Goldwasser | A61N 1/0476 |
| 2019/0262212 A1* | 8/2019 | Schroeder | A61H 1/0296 |

FOREIGN PATENT DOCUMENTS

WO WO-2018039602 A1 * 3/2018 ........... A61N 1/0456

* cited by examiner

*Primary Examiner* — Tammie K Marlen
(74) *Attorney, Agent, or Firm* — Boyle Fredrickson, S.C.

(57) ABSTRACT

Electrical stimulation of specific facial and lingual nerves creates a more sustained pulsatility activity compared to stimulation of other cranial nerves. Pulsatility of arteries has intrinsic time constraints related to the time for vasodilation/constriction and time to return to baseline ($T_{BL}$) after electrical stimulation which may affect the pulsatility response. Control of temporal patterning and the stimulation waveform maximizes the physiological response to cerebral pulsatility and its resulting effects on cerebral spinal fluid penetration into the brain parenchyma for a multitude of therapeutic uses including clearing misfolded proteins and/or administered pharmacological agents, diluting endogenous neurochemical concentrations within the brain, and reducing non-synaptic coupling.

18 Claims, 4 Drawing Sheets

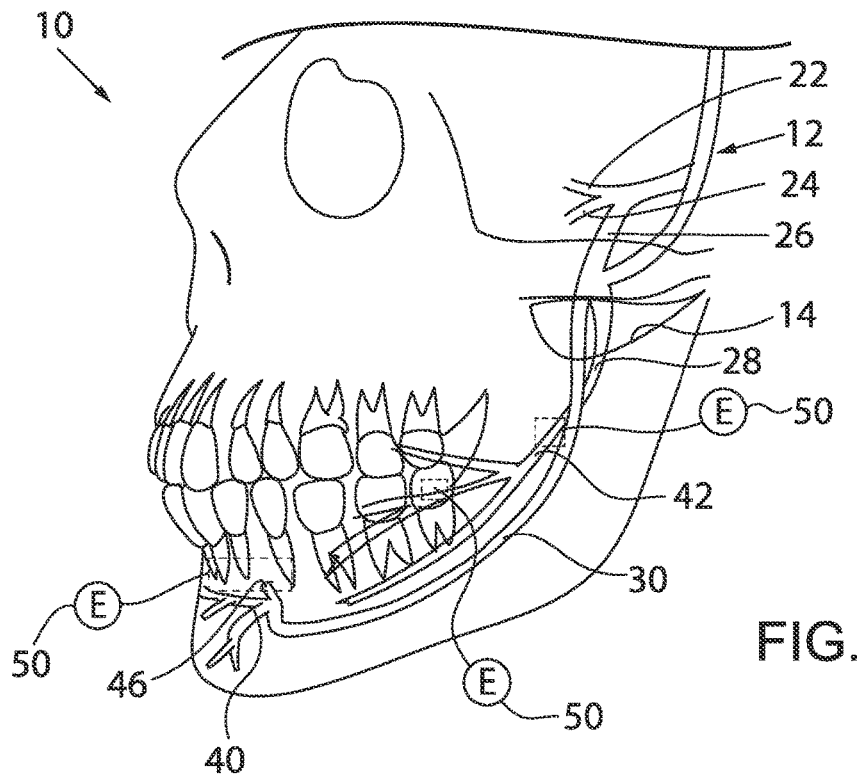
FIG. 1
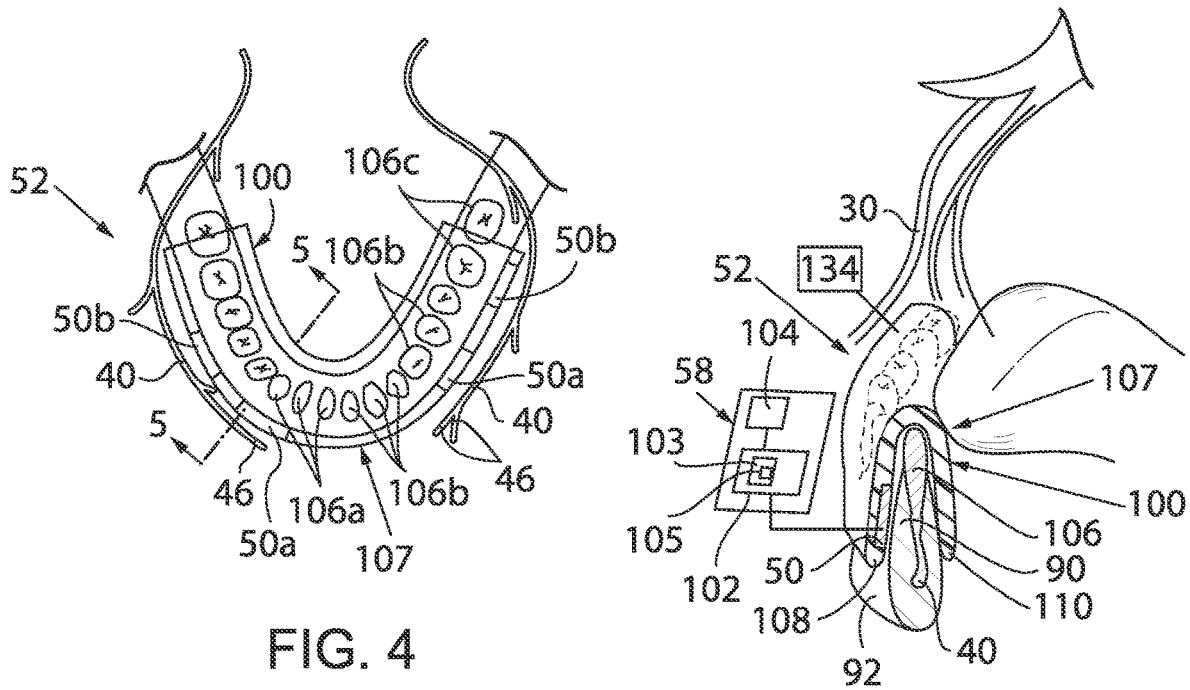
FIG. 4
FIG. 5

PENETRATION OF CEREBRAL SPINAL FLUID INTO THE BRAIN PARENCHYMA USING TEMPORALLY PATTERNED NEUROMODULATION

CROSS-REFERENCE TO RELATED APPLICATIONS

This application is a continuation of U.S. application Ser. No. 16/935,386, filed Jul. 22, 2020, issued as U.S. Pat. No. 11,395,914, which claims the benefit of U.S. Provisional Application No. 62/884,002, filed Aug. 7, 2019, both of which are hereby incorporated by reference.

STATEMENT REGARDING FEDERALLY SPONSORED RESEARCH OR DEVELOPMENT

This invention was made with government support under N66001-17-2-4010 awarded by the DOD/DARPA. The government has certain rights in the invention.

BACKGROUND OF THE INVENTION

The present invention relates to electrical stimulation of target nerves to enhance waste clearance in the brain.

The central nervous system (CNS) lymphatic system is made up of multiple components and pathways including the glymphatic system. The glymphatic system (or glymphatic clearance pathway) is a macroscopic waste clearance system for the vertebrate CNS utilizing a unique system of perivascular tunnels formed by glial cells to promote efficient elimination of soluble and insoluble proteins and metabolites from the CNS. The pathway provides a para-arterial influx route for cerebral spinal fluid (CSF) to travel in the perivascular space surrounding descending vasculature and enter the brain parenchyma through AQP4 channels, and a clearance mechanism via convective movement of interstitial fluid (ISF) for extracellular solutes such as misfolded proteins and unwanted metabolites to be removed from the brain.

The aggregation of pathogenic proteins β-amyloid, α-synuclein, and C-tau in the brain may cause the deleterious effects of numerous diseases and disorders such as traumatic brain injury/chronic traumatic encephalopathy, epilepsy, Alzheimer's disease, and Parkinson's disease. Removal of these pathogenic proteins has been found to have substantial therapeutic benefit, for example, in treating traumatic brain injury/chronic traumatic encephalopathy, epilepsy, Alzheimer's disease, and Parkinson's disease.

Increasing the penetration of CSF into the brain parenchyma can serve many therapeutic purposes, including diluting endogenous neurochemical transmitter concentrations within the brain, altering the clearance rates of drugs delivered orally that penetrate through the blood-brain barrier or delivered via a catheter system to the brain, and reducing non-synaptic coupling between neurons to treat diverse conditions leading to increased neural activity including anxiety disorders, tremor, and seizure.

Transport of CSF along the periarterial spaces into the brain parenchyma and into the cervical and thoracic lymph nodes is driven by cerebral arterial pulsation to the brain. It has previously been found that ligation of the carotid artery or administration of a central sympatholytic such as dobutamine can alter the pulsatility of the cerebral vasculature to drive CSF movement in the associated perivascular space.

SUMMARY OF THE INVENTION

The present inventors have found that electrical stimulation of easily accessible neural inputs located outside of the brain and amenable to minimally invasive or non-invasive stimulation strategies can induce cardiovascular and respiratory changes, dilate arterial vessels and increase the pulsatility (change in the vessel diameters over time relative to a mean vessel diameter) of penetrating arterial vessels in the brain thus leading to increased clearance of misfolded proteins from the brain. Specifically, electrical stimulation of cranial nerves or local areas around the cranial nerves may selectively cause oscillations in pressure and dilation of arteries that help to improve waste clearance in the brain. However, these methods are limited by the body's compensation responses that quickly habituate these effects over time and do not maintain a sustained response when nerves are continuously and repeatedly electrically stimulated. In this respect, continuous stimulation of the cranial nerves only causes brief transient changes in blood flow.

The present inventors recognize that pulsatility of arteries has intrinsic time constraints related to the time for vasodilation/constriction and time to return to baseline ($T_{BL}$) after electrical stimulation, which may affect the pulsatility response. In this respect, these time constraints for stimulation induced vasodilation/constriction and subsequent return to baseline define the maximum and minimum changes to pulsatility. The present invention provides control of temporal patterning and the stimulation waveform in order to maximize the physiological response to cerebral pulsatility and its resulting effects on brain waste clearance. Thus, the electrical stimulation is temporally patterned to generate multiple vasodilation/constriction pulses in succession to optimize and sustain the pulsating action to continuously drive CSF into the brain parenchyma over long periods of time.

Electrical stimulation of specific cranial nerves such as the branches of the trigeminal nerve, i.e., buccal and lingual branch nerves, and the facial nerve creates a more sustained pulsatility activity compared to stimulation of other cranial nerves. One possible explanation for this is that the facial and trigeminal nerves have direct sympathetic/parasympathetic innervation of the cerebral vasculature through several routes, including through the sphenopalatine ganglion (SPG), which are part of neural pathways that directly control the vasodilation/constriction of the cerebral arteries. As a result, the time course for dilation and constriction after a stimulation burst can be quicker than other cranial nerves because the response is quicker than inputs from the spinal cord which change peripheral sympathetic tone or peripheral inputs such as the sciatic nerve that change blood flow primarily through sensory activity mediated neurovascular coupling.

Also, stimulation through pathways that change sympathetic/parasympathetic tone outside the brain dilate the peripheral vasculature outside of the brain. The change in blood flow in the brain is primarily in response to this change in peripheral blood flow to maintain perfusion (there are also occasionally indirect connections between the vagus and facial nerve in some subjects). As vagus nerve stimulation only indirectly influences blood flow in cerebral vasculature, it has a slower time constant between burst of stimulation for changes in flow to return to normal.

Therefore, the present invention provides 1) a unique intraoral device to conveniently and non-invasively activate the facial/trigeminal nerves and 2) unique temporal stimulation patterns to increase CSF flow via the trigeminal/facial nerves, nerve inputs associated with the baroreflex (vagus, aortic depressor, carotid sinus, baroreceptor beds in the bulb, aorta), and peripheral nerve inputs not clearly associated with the baroreflex (median nerve, sciatic nerve, tibial nerve, spinal cord).

1) A Unique Intraoral Device to Conveniently and Non-Invasively Activate the Facial/Trigeminal Nerves Specifically, the present invention provides an electrical stimulation device for improving waste clearance through the perivascular system of the blood brain barrier including at least one electrode configured to stimulate a facial nerve; an electrical generator generating a carrier wave having a carrier frequency stimulating the perivascular system into increased CSF/ISF flow; a modulator receiving the carrier wave and a modulation wave to modulate the carrier wave for application to at least one electrode; and an electrical modulation generator generating the modulation wave having a predetermined periodicity providing a first period of stimulation of the perivascular system and a second period of relaxation of the perivascular system, the predetermined periodicity selected to increase pulsatility over continuous stimulation of the perivascular system by the carrier frequency.

It is thus a feature of at least one embodiment of the present invention to utilize increased cerebral blood flow through arterial vessels to improve the penetration of cerebrospinal fluid into the brain parenchyma.

The electrode may include a cathode positioned distally with respect to a lingual or facial nerve ending and an anode positioned proximally with respect to the lingual or facial nerve ending. The cathode and the anode may be spaced apart along an axis substantially parallel to the nerve. The cathode and anode may be reversed depending on local anatomy.

It is thus a feature of at least one embodiment of the present invention to generate a circuit of electrical impulses along the nerve fibers.

At least one electrode may be adapted to stimulate at least one of a trigeminal nerve, buccal branch nerve, mental branch nerve and facial nerve.

It is thus a feature of at least one embodiment of the present invention to create stimulus locked changes in cerebral blood flow as compared to stimulation of nerves where habituation occurs.

The at least one electrode may be supported by a mouthpiece engaging a jaw of a user's mouth.

It is thus a feature of at least one embodiment of the present invention to utilize the anatomical consistency of the nerves in the jaw region with respect to the jawbone to easily approximate nerve stimulation locations, for example, through the mental foramen.

The mouthpiece may be comprised of a curved tube having an inner and outer wall flanking a channel receiving an upper or lower dental arch of a user and covering an outer labia gingiva of the teeth. At least one electrode may be supported by an inner surface of the outer wall to contact the labia gingiva.

It is thus a feature of at least one embodiment of the present invention to utilize the hydrated epithelial tissue below the gingiva mucosa to provide a conductive path for more efficient electrical stimulation of nerves.

A cathode electrode may be positioned toward a front of the curved mouthpiece receiving the anterior teeth and an anode electrode is positioned toward a rear of the mouthpiece receiving the premolar teeth. The cathode electrode may be positioned to overlay nerve endings of the mental branch nerve with less than 1 cm distance between the cathode electrode and the nerve endings.

It is thus a feature of at least one embodiment of the present invention to provide precise electrical access to the nerve endings where the nerves are positioned close to the outer epidermis of the epithelial tissue.

The mouthpiece may support a first anode-cathode electrode pair on a left side of the mouthpiece and a second anode-cathode electrode pair on a right side of the mouthpiece.

It is thus a feature of at least one embodiment of the present invention to carry multiple electrode pairs for simultaneous multi-nerve stimulation.

The at least one electrode may be supported by a dental filling inserted within a cavity of the tooth. The at least one electrode may be supported by a dental implant inserted within a jawbone.

It is thus a feature of at least one embodiment of the present invention to utilize precise electrical access to the nerve endings of the molar teeth in close proximity to the roots of the molar teeth.

Sensors detecting salivary biomarkers may indicate a change to CSF flow selected from at least one of the following: amyloid beta peptide, tau protein, lactoferrin, alpha-synuclein, DJ-1 protein, chromogranin A, huntingtin protein, DNA methylation disruptions, and micro-RNA.

It is thus a feature of at least one embodiment of the present invention to provide quick visual indication of improved waste clearance through known biomarkers in the patient's saliva.

Electrodes may be used to record electrophysiological signals to detect changes in low frequency power brain waves that propagate outside the calvarium. Electrodes may also be used to pick up heart rate and heart rate variability.

It is thus a feature of at least one embodiment of the present invention to provide quick visual indication of engagement of the stimulating electrodes with the nerves.

2) Unique Temporal Stimulation Patterns to Increase CSF Flow Via the Trigeminal/Facial Nerves, Nerve Inputs Associated with the Baroreflex (Vagus, Aortic Depressor, Carotid Sinus, Baroreceptor Beds in the Bulb, Aorta), and Peripheral Nerve Inputs not Clearly Associated with the Baroreflex (Median Nerve, Sciatic Nerve, Tibial Nerve, Spinal Cord)

An alternative embodiment of the present invention may provide a method of improving waste clearance through the perivascular system of the blood brain barrier including positioning at least one electrode in close proximity to a nerve; generating a carrier wave having a carrier frequency stimulating the perivascular system into increased CSF/ISF flow; generating the modulation wave having a predetermined periodicity providing a first period of stimulation of the perivascular system and a second period of relaxation of the perivascular system, the predetermined periodicity selected to increase pulsatility over continuous stimulation of the perivascular system by the carrier frequency; and modulating the carrier wave and applying the carrier wave to the electrode.

For stimulation of the facial nerves, trigeminal nerves, and sphenopalatine ganglia the carrier frequency of the carrier wave may be between 25 Hz and 55 Hz and centered around 50 Hz. The modulation wave may have a frequency between 0.5 Hz and 0.1 Hz. The modulation wave may have a time duration ("bursts") of between 1 second and 10 seconds with a pulse interval (unstimulated period between "bursts") between 1 second and 10 seconds.

For stimulation of the vagus nerve, carotid sinus nerve, and baroreceptors the carrier frequency of the carrier wave may be between 20 Hz and 50 Hz and centered around 30 Hz. The modulation wave may have a frequency between ⅟₄₅ Hz and ⅟₁₈₀ Hz. The modulation wave may have a time duration ("bursts") of between 15 second and 60 seconds and around 30 seconds with a pulse interval (unstimulated period between "bursts") between 30 seconds and 120 seconds and around 60 seconds.

For stimulation of the sciatic nerve and peripheral nerve the carrier frequency of the carrier wave may be between 20 Hz and 55 Hz and centered around 50 Hz. The modulation wave may have a frequency between ⅟₃₀₀ Hz and ⅟₅₄₀ Hz. The modulation wave may have a time duration ("bursts") of between 1 minute and 4 minutes and around 3 minutes with a pulse interval (unstimulated period between "bursts") between 4 minutes and 6 minutes and around 5 minutes.

It is thus a feature of at least one embodiment of the present invention to introduce periods of relaxation into the electrical stimulation parameters to improve recovery processes of the dilated blood vessels.

At least one electrode may be positioned over the mental branch nerve. At least one electrode may be positioned over the inferior alveolar nerve.

These particular objects and advantages may apply to only some embodiments falling within the claims and thus do not define the scope of the invention.

BRIEF DESCRIPTION OF THE DRAWINGS

FIG. 1 is a schematic diagram of a human skull receiving electrical stimulation from electrodes positioned on facial and lingual nerves of the head in the tooth and jaw region in accordance with the present invention;

FIG. 4 is a top plan view of a mouthpiece placed in a user's mouth and over the lower jaw to deliver directed electrical stimulation to mental branch nerves within the oral mucosa;

FIG. 5 is a perspective cutaway view of FIG. 5 showing the mouthpiece placed within the user's mouth and electrodes of the mouthpiece contacting the oral mucosa to stimulate the mental branch nerves;

DETAILED DESCRIPTION OF THE INVENTION

Background—Facial/Trigeminal Nerves

Figure 2:
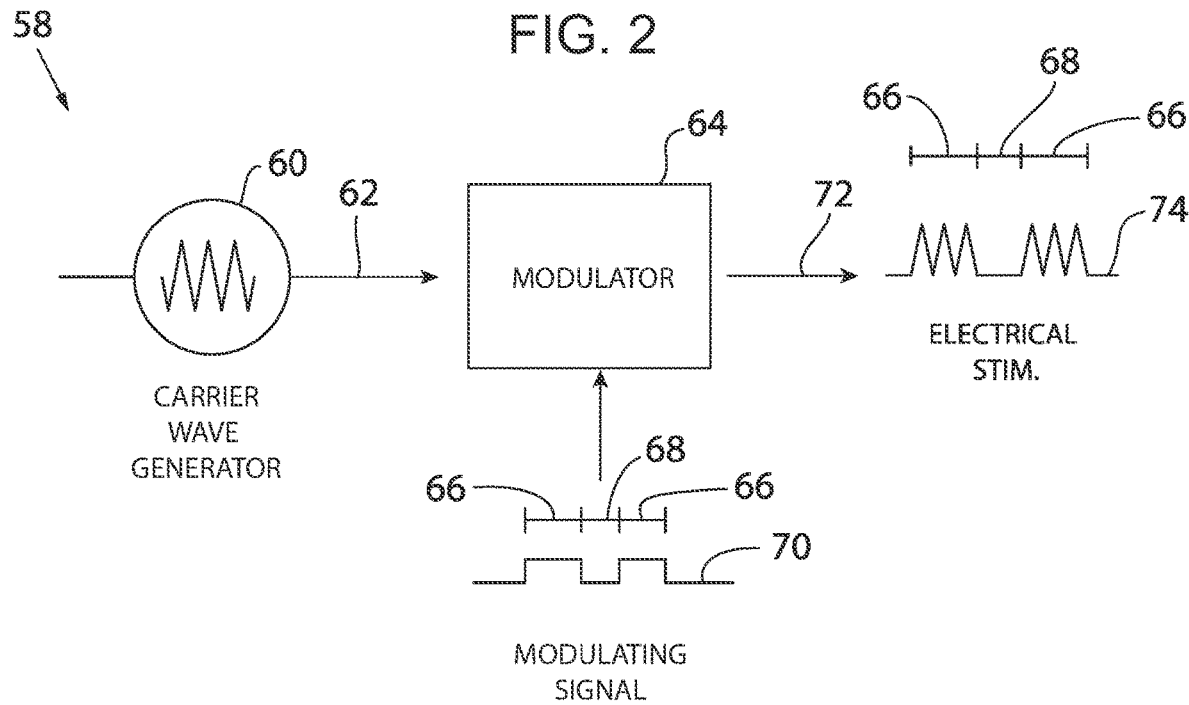
FIG. 2 is a block diagram showing an electrical stimulator modulating a carrier wave to produce a modified electrical signal providing increased CSF flow through arterial vessels to the head and therefore increasing waste clearance.

Referring now to FIG. 1, a typical human skull 10 supports a number of cranial nerves 12 emerging directly from the brain, located within the skull 10, and emerging out through cranial foramina 14, or holes, in the skull 10 to reach their final destinations on the exterior of the skull 10 and around the jaw and neck region. These cranial nerves 12 relay information between the brain and other parts of the body.

The trigeminal nerve 20 (fifth cranial nerve) is the largest of the cranial nerves 12 and provides sensation to the face and various motor functions such as biting and chewing functions. The trigeminal nerve 20 includes three major branches: the ophthalmic nerve (V1) 22, the maxillary nerve (V2) 24, and the mandibular nerve (V3) 26. The mandibular nerve (V3) 26 includes several sub-branches including the lingual nerve 28 and the inferior alveolar nerve 30 that have shown to be particularly receptive to electrical stimulation. The facial nerve (seventh nerve) has also been shown to be receptive to electrical stimulation.

The mental branch nerves 40 are a sub-branch of the inferior alveolar nerve 30 and provide sensation to the front of the chin, lower lip, labial gingiva of the mandibular anterior teeth and the premolars. The buccal branch nerves 42 are a sub-branch of the lingual nerve 28 that provides sensation to the cheek and the second and third molar teeth. The locations of the mental branch nerves 40 and buccal branch nerves 42 in and around the jawbone 44 place the stimulation points or respective nerve endings 46 close to the outermost epidermis of the skin making it an ideal location for electrical stimulation where the distance and impedance between an electrode 50 and the target nerve may be minimized. In this respect lower amounts of electrical energy may be needed to stimulate these sensory nerves compared to nerves located deeper within the skin and which may require more invasive procedures to stimulate the nerves.

Electrodes 50 placed at or proximate to the mental branch nerves 40 and buccal branch nerves 42 allow for electrical stimulation of the respective nerves to therefore elicit a sustained response of the arterial vessels to dilate/constrict in a pulsating manner, as further discussed below. In one embodiment of the present invention, the electrodes 50 are positioned over the mental foramen which may transmit electrical stimulation to the terminal branches of the inferior alveolar nerve and vessels of the mental artery In one embodiment of the present invention, as further discussed below with respect to FIGS. 4 through 6, the electrodes 50 may be a part of an intraoral device 52 placed in the mouth, such as a mouthguard, dental filling or dental implant, to electrically stimulate the inferior alveolar nerve 30 and mental branch nerves 40 located near or around the lower jawbone 44 region. In an alternative embodiment of the present invention, as further discussed below with respect to FIG. 7, the electrodes 50 may be surface electrodes placed on an outer surface of the cheek, or subcutaneous electrodes inserted under the skin in the cheek region to electrically stimulate the buccal branch nerves 42 located in the upper jawbone 44 region and the facial nerves below the cheek.

Temporal Stimulation Patterns to Increase CSF Flow

Referring now to FIG. 2, an optimization of the temporal patterning and stimulation parameters may maximize the cerebral pulsatility and increase the CSF flow to maximize waste clearance from the brain. The pulsatility may be defined as a change in the vessel diameter over time relative to a mean vessel diameter.

Electrical stimulation of the target nerves may be accomplished using an electrical stimulator 58 such as those commercially available from Tucker-Davis Technologies of Alachua, Florida or A-M Systems of Sequim, Washington. The electrical stimulator 58 may include a carrier wave generator 60 having a processor 102 being an electronic computer having a self-contained nonvolatile memory 103 holding an operating program 105 and necessary storage variables as will be described below. The nonvolatile memory 103 may comprise, for example, flash memory and/or read only memory, or other similar nonvolatile memory as context requires, which may store data values to be retained even in the absence of electrical power. The processor 102 may be a STM32 Nulceo board or PIC microcontroller as known in the art.

The processor 102 provides various inputs and output lines communicating, for example, with one or more stored programs 105 stored in non-transitory memory 103 and the carrier wave generator 60 to generate a carrier wave 62 at a carrier frequency and amplitude. In one embodiment, the processor 102 may be external to the intraoral device 52 and communicate wirelessly with the carrier wave generator 60 on the intraoral device 52. In an alternative embodiment, the processor 102 may be mounted on a flexible printed circuit board and incorporated or molded onto the intraoral device 52 to communicate with the carrier wave generator 60 on the intraoral device 52 via a wired connection.

Figure 3:
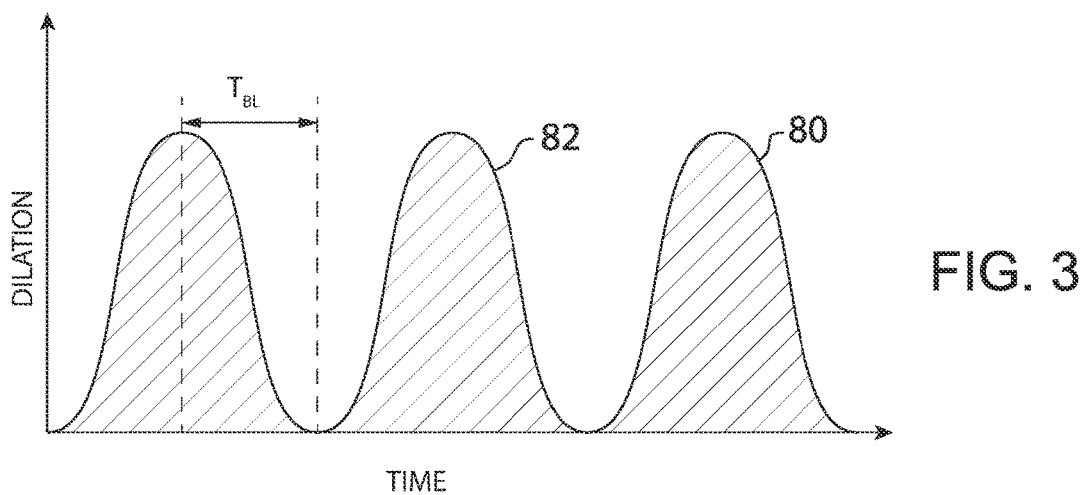
FIG. 3 is a graph showing a magnitude of vasodilation/constriction of arterial vessels relative to a mean vessel diameter as a function of a time to return to baseline ($T_{BL}$) at a given electrical stimulation frequency and duty cycle.

The carrier wave 62 is delivered to a modulator 64 modulating the carrier wave 62 amplitude according to a modulating signal 70. In a simplest configuration, modulator 64 passes the carrier wave 62 without modification during a first stimulation period 66 and/or turns off the carrier wave 62 during a second period 68. In this case, the modulating signal 70 may be a discontinuous waveform such as a pulse or square wave. As is understood in the art, signal modulation by the modulator 64 may provide an envelope of the peaks of the carrier wave 62, the latter being of much higher frequency than the modulating signal 70. Although the modulating signal 70 is shown as a square wave in FIG. 2, the modulating signal 70 may also be a smooth curve as shown in FIG. 3. Referring also to FIG. 3, the stimulation parameters of the modulating signal 70 may be empirically set in order to maximize CSF flow through arterial vessels to the brain. This set point may be established, for example, by monitoring a set of patients being scanned in a computed tomography (CT) scanner or magnetic resonance imaging (MRI) scanner with contrast media to detect CSF/ISF flow and adjusting the stimulation time and relaxation time to maximize the area 80 beneath the CSF/ISF flow curve 82. These settings may then be used generally for all patients or may be optimized for particular patient classes such as by age, height and weight, and sex. Ideally the set point will provide a relaxation time (pulse interval 68) that is no less than the time to return to baseline ($T_{BL}$) measured after brief periods of stimulation (pulse duration 66). While the inventors do not wish to be bound by a particular theory, it is believed that the accommodation or acclamation of the tissue to the stimulation effectively limits the clearance when continuous stimulation is provided as understood in the prior art. By interleaving stimulation (pulse duration 66) with periods of rest (pulse interval 68), recovery processes of the glymphatic and meningeal lymphatic system may be accommodated to allow greater clearance long run.

Thus, the dilation/constriction of arterial vessels at various modulating signal frequencies may be compared to maximize the area 80 under the curve 82 of FIG. 3, for example, slow, large amplitude changes in clearance (produced by prolonged carrier frequency stimulation) may be compared with faster, smaller amplitude changes in clearance (produced by shortened carrier frequency stimulation) to provide the greatest increases in CSF flow over time in the perivascular space. Similar comparisons may be done with respect to the spacing between stimulation provided by the relaxation period.

The following are exemplary embodiments of modulating signal frequencies for specific target nerves optimized to create a full pulse without attenuating the peak flow response but accelerating the return to baseline.

Example 1: Facial Nerves, Trigeminal Nerves, and Sphenopalatine Ganglia

Figure 8:
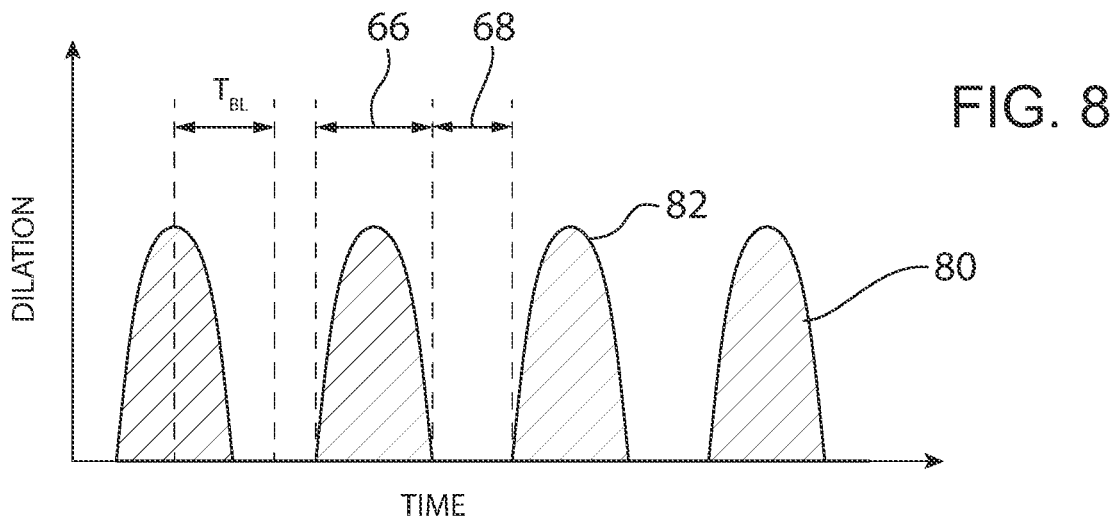
FIG. 8 is a graph, similar to FIG. 3, showing a magnitude of vasodilation/constriction of arterial vessels relative to a mean vessel diameter as a function of a time to return to baseline ($T_{BL}$) at an optimal electrical stimulation frequency and duty cycle for stimulation of the facial nerves, trigeminal nerves, and sphenopalatine ganglia.

Referring to FIG. 8, the carrier wave 62 may be a single frequency waveform (e.g. a sine wave) with the frequency of the carrier wave 62 less than 75 hertz, and between 20 hertz and 60 hertz and preferably between 25 hertz and 55 hertz, with the preferred range centered around 50 hertz. At higher frequencies (75 Hz or above), habituation occurs before peak flow change is obtained, causing a weaker effective pulse.

In some embodiments, the modulating signal 70 of the modulator 64 may be a single frequency, monophasic signal such as a sine wave creating "bursts" of electrical stimulation. The frequency of the modulating signal 70 is preferably between 0.5 hertz and 0.1 hertz. The modulating signal 70 may provide electrical stimulation 72 with electrical pulses 74 having a time duration 66 between 1 second and 10 seconds, and preferably 5 seconds, and pulse intervals 68 between 1 second and 10 seconds, and preferably 5 seconds between pulses. Although the inventors do not wish to be bound by a particular theory, the introduction of a relaxation period where there is no stimulation (pulse interval 68) counterintuitively increases total clearance.

In one embodiment of the present invention, the carrier wave 62 may have a frequency between 5 kilohertz and 300 kilohertz for non-invasive stimulation. The carrier wave 62 may have a current amplitude of less than 100 microamps for invasive stimulation and less than 40 milliamps for non-invasive stimulation and a voltage controlled to achieve this current per current control known in the art. The modulating signal 70 may have a period between 15 microseconds and 5 milliseconds.

Although electrical stimulation has been shown and described with respect to stimulating the facial nerves and trigeminal nerves, it is understood that the temporal patterning of the present invention may also be applied to other target nerves identified as providing increased CSF flow, and as further described below with respect to Examples 2 and 3.

Example 2: Vagus Nerve, Carotid Sinus Nerve, and Baroreceptor

Changes in cerebral vasculature blood flow driven by stimulation of baroreflex inputs such as the vagus nerve, aortic depressor nerve, carotid sinus nerve, and carotid sinus bulb/aortic arch are not driven by direct connection to the cerebral vasculature. Instead, they dilate the peripheral arteries through activation of the baroreflex pathway, and the cerebral vessels then react to maintain constant perfusion in the brain. As this response is indirect it has a slower time constant for temporal patterning. Stimulation must be maintained longer to cause this indirect effect on cerebral vasculature, and the habituation period is driven by the entire system finding a new set point for homeostasis. The longer rest period is needed to allow the neural inputs indirectly governing the peripheral vasculature response to recover.

Figure 9:
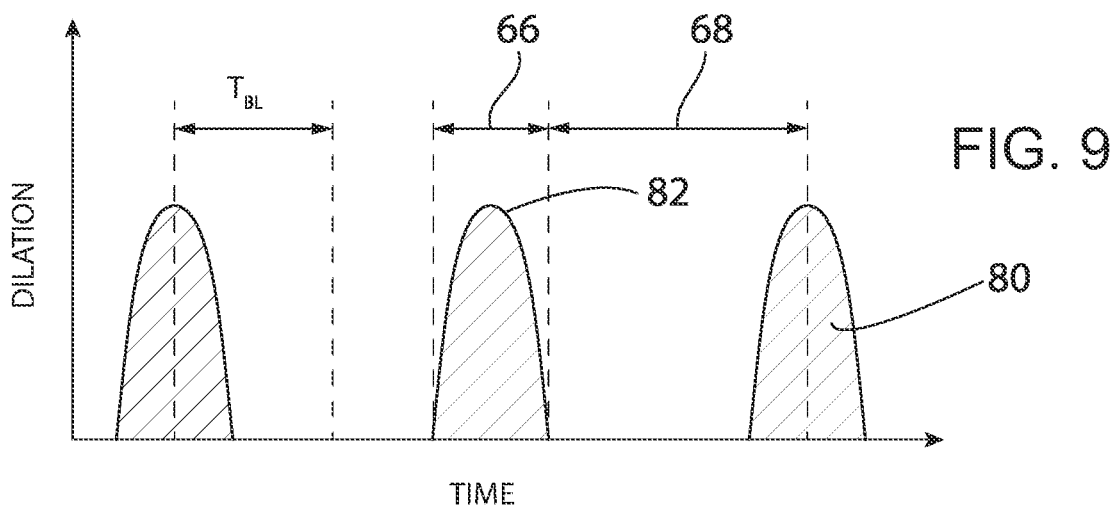
FIG. 9 is a graph, similar to FIG. 3, showing a magnitude of vasodilation/constriction of arterial vessels relative to a mean vessel diameter as a function of a time to return to baseline ($T_{BL}$) at an optimal electrical stimulation frequency and duty cycle stimulation of the vagus nerve, carotid sinus nerve, and baroreceptors.

Referring to FIG. 9, the carrier wave 62 may be a single frequency waveform (e.g. a sine wave) where the frequency of the carrier wave 62 may be less than 75 hertz, and between 20 hertz and 75 hertz and preferably between 25 hertz and 50 hertz, with the preferred range centered around 30 hertz. At higher frequencies (75 Hz or above), neural habituation occurs before peak flow change is obtained and/or unwanted chemoreceptor activation can occur, causing a weaker effective pulse.

In some embodiments, the modulating signal 70 of the modulator 64 may be a single frequency, monophasic signal such as a sine wave creating "bursts" of electrical stimulation. The frequency of the modulating signal 70 is preferably between $\frac{1}{45}$ hertz and $\frac{1}{180}$ hertz. The modulating signal 70 may provide electrical stimulation 72 with electrical pulses 74 having a time duration 66 between 15 seconds and 60 seconds, and preferably 30 seconds, and pulse intervals 68 between 30 seconds and 120 seconds between pulses, and preferably 60 seconds. Although the inventors do not wish to be bound by a particular theory, the introduction of a relaxation period where there is no stimulation (pulse interval 68) counterintuitively increases total clearance.

In one embodiment of the present invention, the carrier wave 62 may have a frequency between 5 kilohertz and 300 kilohertz for non-invasive stimulation. The carrier wave 62 may have a current amplitude of less than 100 microamps for invasive stimulation and less than 40 milliamps for non-invasive stimulation and a voltage controlled to achieve this current per current control known in the art. The modulating signal 70 may have a period between 15 microseconds and 5 milliseconds.

Example 3: Sciatic Nerve and Peripheral Nerve

The mechanism by which peripheral nerves influence blood flow in the cerebral vasculature blood flow that are not mediated by the baroreflex is by increasing activity in specific regions of the brain. This increase in brain activity increases metabolic demand in these areas, and the vasculature of the brain compensates to increase supply, known as neurovascular coupling. Consequently, the temporal patterning needed to optimize pulsatility of the cerebral vasculature is slower than described for facial/trigeminal nerves that directly dilate cerevasculature or for baroreflex mediated response. This creates the smallest increase in pulsatility of the neural input options described. However, as neural inputs such as the sciatic are superficial, they are often easier to engage with non-invasive or minimally invasive surgical strategies. There is a delay for the blood flow to respond to the increased metabolic demand, and the rest period is necessary to allow metabolic demand/supply to return to normal before activating another pulse sequence.

Figure 10:
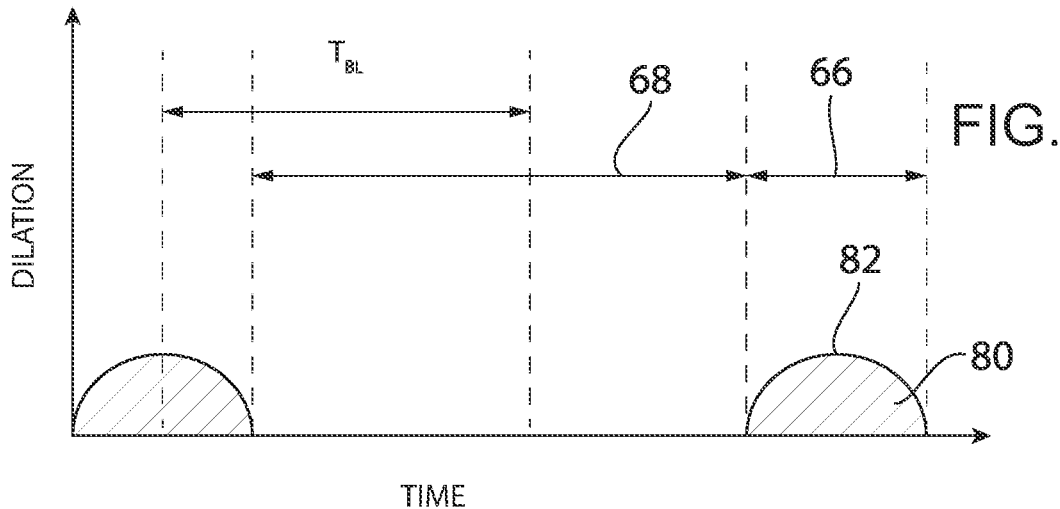
FIG. 10 is a graph, similar to FIG. 3, showing a magnitude of vasodilation/constriction of arterial vessels relative to a mean vessel diameter as a function of a time to return to baseline ($T_{BL}$) at an optimal electrical stimulation frequency and duty cycle for stimulation of the sciatic nerve and peripheral nerve.

Referring to FIG. 10, the carrier wave 62 may be a single frequency waveform (e.g. a sine wave) with the frequency of the carrier wave 62 may be less than 75 hertz, and between 20 hertz and 60 hertz and preferably between 25 hertz and 55 hertz, with the preferred range centered around 50 hertz.

In some embodiments, the modulating signal 70 of the modulator 64 may be a single frequency, monophasic signal such as a sine wave creating "bursts" of electrical stimulation. The frequency of the modulating signal 70 is preferably between $\frac{1}{300}$ hertz and $\frac{1}{540}$ hertz. The modulating signal 70 may provide electrical stimulation 72 with electrical pulses 74 having a time duration 66 between 1 minute and 4 minutes, and preferably 3 minutes, and pulse intervals 68 between 4 minutes and 6 minutes between pulses, and preferably 5 minutes. Although the inventors do not wish to be bound by a particular theory, the introduction of a relaxation period where there is no stimulation (pulse interval 68) counterintuitively increases total clearance.

The invention contemplates that at some point it may be possible to provide real-time sensing of clearance. In that case the processor 102 executing one or more stored programs 105 stored in non-transitory memory 103 may automatically determine a frequency in which pulsatility is maximized by providing variations in the above described parameters and monitoring clearance appropriately. Similarly, the processor 102 may automatically determine a minimum time duration of the electrical pulses required to provide maximum effect.

In this respect, the real-time sensing of clearance, for example, monitoring preictal seizure activity or heart rate, may be used to determine when additional electrical stimulation to the stimulation device is needed and further administered to the patient, or to alert the patient or medical professional to deliver electrical stimulation to the patient.

The CSF/ISF flow may be monitored using known imaging modalities such as CT scan, MRI scan, and panoramic x-ray during electrical stimulation. It is understood that other physiological factors may also be monitored to determine the effectiveness of stimulation parameters, such as changes to heart rate, respiratory rate, or presence of certain biomarkers in the patient's blood or saliva as further described below. These physiological factors may be measured using, for example, neuroimaging techniques (e.g., panoramic x-ray, computerized topography (CT) scan, diffuse optical imaging (DOI), event-related optical signal (EROS), magnetic resonance imaging (MM), functional magnetic resonance imaging (fMRI), magnetoencephalography (MEG), positron emission tomography (PET), single-photon emission computed tomography (SPECT), and cranial ultrasound), cognitive function testing (e.g., learning tests and memory tests), motor function testing, sensory function testing, biopsy, CSF testing, blood testing and/or genetic testing.

Intraoral Device to Activate the Facial/Trigeminal Nerves

Referring to FIGS. 4 and 5, the electrical stimulation 72 of facial and lingual nerves may be facilitated by electrodes 50 placed on an intraoral device 52 placed within the mouth. The intraoral device 52 may be used to conveniently and consistently position the electrodes 50 at specific locations in the mouth to provide electrical stimulation 72 to target nerves. For example, the electrodes 50 may be placed in close proximity to the mental foramen and/or the inferior alveolar nerve 30 and mental branch nerves 40, accessible through the labial gingiva 90 and alveolar mucosa 92 of the mouth as described below. The hydrated epithelial tissue of the labial gingiva 90 and alveolar mucosa 92 assist to provide a conductive path to the target nerves.

In one embodiment of the present invention, the intraoral device 52 is a mouthpiece 100 receivable into a patient's mouth and configured to carry the electrical circuitry of the electrical stimulator 58 as described above with respect to FIG. 2, and generally including the processor 102 and battery power supply 104 (for example, including rechargeable lead acid or lithium ion batteries) for delivery of electrical stimulation 72 to the electrodes 50 within the mouth.

The mouthpiece 100 may be a mouthguard-type device made of a medical grade, non-conductive material such as acrylic, poly (vinyl acetate-ethylene) copolymer clear thermoplastic, polyurethane, laminated thermoplastic, or other medical grade plastic. The mouthpiece 100 provides a cover that extends upward or downward over at least part of the teeth 106, labial gingiva 90, and optionally, alveolar mucosa 92 in a manner which would support electrodes 50 close to the labial gingiva 90, and optionally, alveolar mucosa 92 overlaying the target nerves. The mouthpiece 100 may be custom molded to fit a specific patient's mouth, teeth 106 and jawbone 44. For example, the mouthpiece 100 may be 3D printed based on a CT scan of the jawbone 44. Alternatively, the mouthpiece 100 may be manufactured at various predetermined sizes in a manner which would allow the mouthpiece 100 to fit different sized mouths, teeth 106 and jawbones 44 of patients.

The mouthpiece 100 may be molded to receive both the upper and lower dental arches of a patient's mouth when the jawbone 44 is closed and the teeth 106 bite down on the mouthpiece 100, similar to a conventional sports mouthguard. However, it may be desired that the mouthpiece 100 also be formed of separate upper and lower components which may be worn on one or both of the upper or lower dental arches of the patient's mouth, similar to a conventional dental retainer, so that the jawbone 44 can be opened and closed when the mouthpiece 100 is worn.

In an exemplary embodiment showing a lower component mouthpiece 100, as illustrated in FIGS. 4 and 5, the mouthpiece 100 may be an arcuate tube 107 having a circular or oval cross section cut along a generally longitudinal plane to define a downwardly extending arch with a downwardly extending outer sidewall 108 and inner sidewall 110 extending generally parallel and flanking outer and inner sides of the lower teeth 106 respectively. A bottom of the arcuate tube 107 is open to reveal a channel 112 sized and shaped to receive the lower teeth 106 of the patient's mouth. The arcuate tube 107 extends over a top of the lower teeth 106 with the outer sidewall 108 extending downwardly along an outer side of the lower teeth 106 to partially cover at least part of the labial gingiva 90 and optionally the alveolar mucosa 92 on an outside of the lower dental arch, while the inner sidewall 110 extends downwardly along a rear side of the lower teeth 16 and may at least partially cover the labial gingiva 90 and alveolar mucosa 92 on an inside of the lower dental arch. It is understood that the inner sidewall 110 does not need to extend as far downwardly as the outer sidewall 108 and is meant primarily to support the arcuate tube 107 over the lower teeth 106.

The mouthpiece 100 may have an arcuate length extending rearwardly along a curve generally correlating with the lower dental arch of the patient. The mouthpiece 100 may curve at a front end and extend rearwardly along left and rights sides of the lower jawbone 44 to cover the mandibular anterior teeth 106a and the premolars 106b. The mouthpiece 100 may further extend rearwardly along left and rights sides of the lower jawbone 44 to optionally further cover the second and third molar teeth 106c.

It is understood that an alternative embodiment of the mouthpiece 100 that receives both the upper and lower dental arches of a patient's mouth when the jawbone 44 is closed and the teeth 106 bite down on the mouthpiece 100 may similarly provide outer and inner sidewalls 108, 110 flanking the lower teeth 106.

The outer and inner sidewalls 108, 110 of the mouthpiece 100 may support the electrical circuitry components of the electrical stimulator 58 such as the processor 102 and the battery power supply 104. The processor 102 and battery power supply 104 may be embedded within the sidewalls 108, 110 of the mouthpiece 100 so that they do not interfere with the fit of the mouthpiece 100 over the lower dental arch. The processor 102 and battery power supply 104 may communicate with the electrodes 50 supported by the outer sidewall 108 to deliver the modulated electrical stimulation signal 72 to the electrodes 50 as described above.

The battery power supply 104 may provide power to the electrical stimulator 58 in a manner which allows for current delivery to the electrodes 50. It is understood that an external power supply may also be used to deliver power to the electrical stimulator 58 in addition to or instead of the battery power supply 104. It is also understood that the electrical stimulator 58 may be positioned outside of the mouth and communicate remotely with a controller and electrodes 50 of the mouthpiece 100.

A position of the electrodes 50 on the walls of the mouthpiece 100 may be determined by a location of the mental branch nerves 40 and nerve endings 46 in the mouth. In this respect, medical imaging may be used to locate the position of the mental branch nerves 40 in the mouth and to aid in placement of the electrodes 50 on the mouthpiece 100. Specifically, when the mouthpiece 100 is positioned in the patient's mouth, the electrodes 50 are desirably positioned on an interior side of the front sidewall 108 proximate the mandibular anterior teeth 106a and the premolars 106b to abut or be placed in close proximity to the labial gingiva 90 and alveolar mucosa 92 on the outside of the lower dental arch in a manner which provides stimulation to the mental branch nerves 40.

The electrodes 50 may include a stimulating cathode electrode 50a placed close to the desired stimulation site, for example, near the nerve endings 46 of the mental branch nerves 40. An anode electrode 50b may then be placed proximal to the cathode electrode 50a with respect to the nerve endings 46. In this respect, the electrical current flows from the anode electrode 50b to the cathode electrode 50a so that the nerve endings 46 receives the stimulus and propagates an action potential upstream through the mental branch nerves 40. The cathode electrode 50a and anode electrodes 50b are spaced apart along an axis generally parallel to the course of the mental branch nerves 40.

Medical imaging may be used to facilitate precise placement of the cathode electrode 50a close to the nerve ending and the precise placement of the anode electrode 50b upstream from the cathode electrode 50a and proximal to the nerve ending 46. The cathode electrode 50a may be placed less than 2 cm or less than 1 cm from the mental branch nerve ending 46 and the anode electrode 50b may be placed less than 3 cm or less than 2 cm upstream from the cathode electrode 50a along the mental branch nerves 40.

It is understood that the pair of communicating electrodes, i.e., the cathode electrode 50a and anode electrode 50b, may stimulate at least one of the left and right side mental branch nerves 40 of the mouth and the mouthpiece 100 may include more than one pair of anode and cathode electrodes 50a, 50b to stimulate both the left and right mental branch nerves 40 of the left and right sides of the mouth. It is also understood that more than two pairs of anode and cathode electrodes 50a, 50b may be carried by the mouthpiece 100 to stimulate various areas along the mental branch nerves 40. In some embodiments, changing the phase of the modulating signal 70 to different mental branch nerves 40 may be used to enhance the stimulation of the mental branch nerves 40 by timing the delivery of the electrical stimulation to the multiple pairs of electrodes. In one embodiment, electrical simulation may be rotated across several electrodes placed across the target nerve, to maximize activation of that nerve without activating nearby nerves responsible for unwanted side effects.

It is understood that an upper component mouthpiece may be described in a similar manner as the lower component mouthpiece described above and shown in FIGS. 4 and 5 whereby the upper component mouthpiece is rotated 180-degrees about a horizontal axis to receive the upper dental arch instead of the lower dental arch and stimulate the superior alveolar nerves of the upper jawbone 44 in a similar manner, as would be understood by one having ordinary skill in the art.

Figure 6:
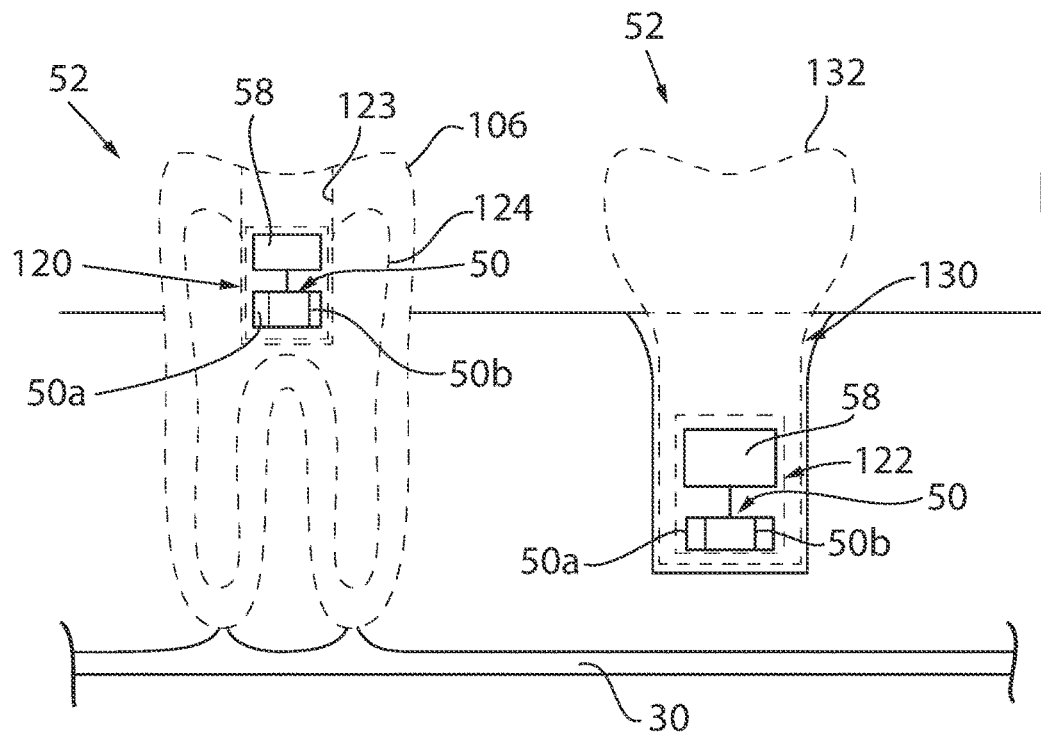
FIG. 6 is a sectional view of a dental filling and dental implant placed within a user's jaw to deliver directed electrical stimulation to, for example, an inferior alveolar nerve of the second and third molars.

Referring now to FIG. 6, in an alternative embodiment of the present invention, the intraoral device 52 may be a dental filling 120 inserted within a cavity or hole of the tooth 106, or a dental implant 122 implanted within a hole of the gums and jawbone 44, to provide electrical stimulation to the inferior alveolar nerve 30 located below the roots of the molar teeth 106.

In one embodiment, the intraoral device 52 may be dental filling 120 inserted within a cavity or hole 123 drilled through a crown of a molar tooth 106 (similar to a root canal procedure) to expose the pulp 124 of the tooth 106 normally carrying nerves and blood vessels from the healthy tooth to nerves and blood vessels outside and below the tooth 106. The dental filling 120 may include the electrical circuitry of the electrical stimulator 58 described above with respect to FIG. 2 and stimulating electrodes 50. The electrodes 50 may include a cathode electrode 50a and anode electrode 50b separated within the dental filling 120 to provide electrical current flow therebetween and provide current flow into the pulp 124 of the tooth 106 thereby stimulating the nerves below the molar tooth 106 (second and third molar teeth 106c) such as the inferior alveolar nerve 30.

In an alternative embodiment, the intraoral device 52 may be a dental implant 122 implanted within a hole 130 within the gums and jawbone 44 caused by a removed or extracted tooth and providing an opening into which the dental implant 122 may be implanted. The dental implant 122 may include the electrical circuitry of the electrical stimulator 58 described above with respect to FIG. 2 and stimulating electrodes 50. The electrodes 50 may include a cathode electrode 50a and anode electrode 50b separated within the dental implant 122 to provide electrical current flow therebetween and to provide current flow to nerves running below the hole 130 (below second and third molar teeth 106c) such as the inferior alveolar nerve 30. As understood in the art, the dental implant 122 may also include an implant crown 132 resembling a real tooth worn over the top of the dental implant 122.

Referring to FIGS. 4 through 6, the intraoral devices 52 described above may include and support biomarker sensors 134 with fluorescent indicators indicating the presence of various analytes from tissue or saliva indicating increased levels of neuronal cytokines indicative of an increase in CSF flow to the brain. For example, amyloid beta peptide, tau protein, lactoferrin, alpha-synuclein, DJ-1 protein, chromogranin A, huntingtin protein, DNA methylation disruptions, and micro-RNA profiles may be detected to show an increase in CSF.

The stimulating electrodes 50 or separate electrodes may be used to record electrophysiological signals to detect changes in low frequency power brain waves that propagate outside the calvarium. The electrodes 50 may also be used to pick up heart rate and heart rate variability as well.

Figure 7:
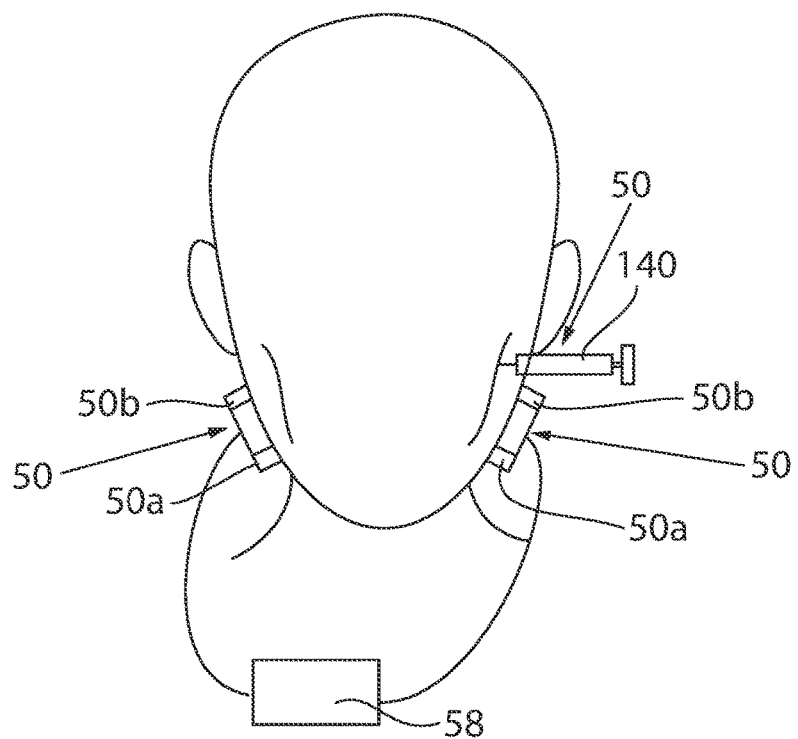
FIG. 7 is a schematic diagram of a human head receiving electrodes on or in a cheek region to deliver directed electrical stimulation to a buccal branch of the lingual nerve within the cheek region.

Referring to FIG. 7, in another embodiment of the present invention, electrical stimulation of facial and lingual nerves may be facilitated by electrodes 50 placed on or within the cheek region. The electrodes 50 may be a surface electrodes or subcutaneous electrodes providing electrical stimulation to the buccal branch nerves 26 located below the skin in the cheek region.

In one embodiment, the electrodes 50 are surface electrode pads placed externally on the user's cheeks overlying the buccal branch nerves 26 to stimulate the buccal branch nerves 26 and/or facial nerves. The electrodes 50 may include a cathode electrode 50a and anode electrode 50b placed externally on the same cheek. Current flow between the anode and cathode electrodes 50a, 50b may provide electrical stimulation of the target nerve. A second set of anode and cathode electrodes 50a, 50b may be placed on the opposite cheek to stimulate the buccal branch nerves 26 and/or facial nerves of the opposite cheek.

In an alternative embodiment, the electrodes 50 may be subcutaneous electrodes inserted beneath the epidermis within the user's cheeks to stimulate the buccal branch nerves 26. The subcutaneous electrodes may be injectable electrodes 50 such as liquid metal electrodes injectable using a syringe 140 and withdrawable from the skin. The injectable electrodes 50 may include a cathode electrode 50a and anode electrode 50b placed under the skin. Current flow between the anode and cathode electrodes 50a, 50b may provide electrical stimulation of the target nerve. The injectable electrodes 50 may be injected into one or both of the cheeks to stimulate the buccal branch nerves 26.

It is understood that the electrical stimulation describe above could also be accomplished with infrared activation, optogenetic activation, and transcranial/transdermal magnetic stimulation, and focused ultrasound.

The above described methods may be used to treat patients with for example depression, anxiety and epilepsy by increasing the influx of CSF into the brain parenchyma. It has been found that an increase in CSF into the brain parenchyma further dilutes endogenous concentrations of neurochemical transmitters/bioactive molecules and reduces ephaptic (non-synaptic) coupling implicated in abnormal circuit behaviors associated with multiple disorders of the nervous system, for example, anxiety disorders, epilepsy, Alzheimer's disease, and Parkinson's disease.

It is understood that the present invention is not limited to the treatment of traumatic brain injury/chronic traumatic encephalopathy, epilepsy, Alzheimer's disease, and Parkinson's disease and the like and may also be used to treat other conditions and disorders such as hydrocephalus caused by a buildup of CSF in the brain parenchyma by increasing the clearance of CSF through the brain. Also, clearance of orally administered drugs that cross the blood brain barrier, or drugs/biomolecules that are infused via an injection/catheter, can be modulated by changing the CSF flow rate.

In addition to increasing pulsatility, electrical stimulation of the nerves as described above has been found to induce neuroplasticity or cortical plasticity and introduce and modify brain wave oscillation frequency useful for treating neuro-psychiatric disorders. For example, brain wave oscillations may be increased to natural brain wave frequencies, e.g., 8 to 13 hertz, which may be lower in older adults experiencing memory difficulties, and activation of circuitry through the trigeminal sensory nuclei to create broad neurochemical changes in the brain mediated by cross connectivity to the nucleus of the solitary tract (NTS) to enhance plasticity in many conditions such as stroke and tinnitus. The NTS has inputs to locus coeruleus, raphae nucleus, and nucleus basalis which are responsible for most norepinephrine, serotonin, dopaminergic, and cholinergic projections to the rest of the brain. Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "an electronic computer" and "a processor" or "the microprocessor" and "the processor," can be understood to include one or more of these devices that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

References to "a processor" should be understood to include electronic computers, microprocessors, microcontrollers, FPGA devices, ASIC devices and similar programmable or program defined electronic circuits and collections of such devices that can communicate in a stand-alone and/or a distributed environment(s), and can thus be configured to communicate via wired or wireless communications with other processors. Furthermore, references to memory, unless otherwise specified, can include one or more processor-readable and accessible memory elements and/or components that can be internal to the processor or external to the processor and accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An electrical stimulation device for improving waste clearance through a perivascular system comprising:
   an intraoral device receivable within a human mouth;
   at least one electrode supported by the intraoral device configured to stimulate a facial nerve;
   an electrical generator generating a carrier wave delivered to the at least one electrode having a carrier frequency, the electrical generator stimulating the perivascular system into increased CSF and ISF flow; and
   at least one sensor attached to the intraoral device configured to detect biomarkers within the human mouth indicating an increased cerebral spinal fluid (CSF) and interstitial fluid (ISF) flow.

2. The electrical stimulation device of claim 1 wherein the biomarkers are analytes of tissue or saliva.

3. The electrical stimulation device of claim 2 wherein the analytes are at least one of amyloid beta peptide, tau protein, lactoferrin, alpha-synuclein, DJ-1 protein, chromogranin A, huntingtin protein, DNA methylation disruptions, and micro-RNA profiles.

4. The electrical stimulation device of claim 2 wherein the at least one sensor is configured to detect increased levels of neuronal cytokines.

5. The electrical stimulation device of claim 1 wherein the biomarkers are at least one of a brain wave frequency and heart rate further indicating an increased cerebral spinal fluid (CSF) and interstitial fluid (ISF) flow.

6. The electrical stimulation device of claim 5 wherein the at least one electrode is configured to detect changes in low brain wave frequency.

7. The electrical stimulation device of claim 1 wherein the at least one electrode is adapted to stimulate at least one of a trigeminal nerve, buccal branch nerve, mental branch nerve and facial branch nerve.

8. The electrical stimulation device of claim 1 wherein the intraoral device is a mouthpiece configured to engage a jaw of a user's mouth.

9. An electrical stimulation device for improving waste clearance through a perivascular system comprising:
   an intraoral device receivable within a human mouth;
   at least one electrode supported by the intraoral device configured to stimulate a facial nerve;
   an electrical generator generating a carrier wave delivered to the at least one electrode having a carrier frequency, the electrical generator stimulating the perivascular system into increased CSF and ISF flow; and
   at least one sensor supported by the intraoral device configured to detect biomarkers indicating an increased cerebral spinal fluid (CSF) and interstitial fluid (ISF) flow;
   wherein the intraoral device is a dental filling configured to be inserted within a cavity of a tooth.

10. An electrical stimulation device for improving waste clearance through a perivascular system comprising:
   an intraoral device receivable within a human mouth;
   at least one electrode supported by the intraoral device configured to stimulate a facial nerve;
   an electrical generator generating a carrier wave delivered to the at least one electrode having a carrier frequency, the electrical generator stimulating the perivascular system into increased CSF and ISF flow;
   at least one sensor supported by the intraoral device configured to detect biomarkers indicating an increased cerebral spinal fluid (CSF) and interstitial fluid (ISF) flow;
   an electrical modulation generator configured to generate a modulation wave having a predetermined periodicity providing a first period of stimulation of the perivascular system and a second period of relaxation of the perivascular system, the predetermined periodicity selected to increase pulsatility over continuous stimulation of the perivascular system by the carrier frequency; and
   a modulator receiving the carrier wave and the modulation wave and modulating the carrier wave for application to the at least one electrode.

11. A method of improving waste clearance through a perivascular system comprising:
   positioning at least one electrode supported by an intraoral device in close proximity to a facial nerve;
   generating a carrier wave having a carrier frequency stimulating the perivascular system into increased cerebral spinal fluid (CSF) and interstitial fluid (ISF) flow;
   applying the carrier wave to the at least one electrode; and
   detecting biomarkers indicating an increased cerebral spinal fluid (CSF) and interstitial fluid (ISF) flow.

12. The method of claim 11 wherein the biomarkers are analytes of tissue or saliva.

13. The method of claim 12 wherein the analytes are at least one of amyloid beta peptide, tau protein, lactoferrin, alpha-synuclein, DJ-1 protein, chromogranin A, huntingtin protein, DNA methylation disruptions, and micro-RNA profiles.

14. The method of claim 12 wherein the at least one sensor is configured to detect increased levels of neuronal cytokines.

15. The method of claim 11 wherein the biomarkers are at least one of a brain wave frequency and heart rate further indicating an increased cerebral spinal fluid (CSF) and interstitial fluid (ISF) flow.

16. The method of claim 15 wherein the at least one electrode is configured to detect changes in low brain wave frequency.

17. The method of claim 11 wherein the facial nerve is at least one of a trigeminal nerve, buccal branch nerve, mental branch nerve and facial branch nerve.

18. The method of claim 11 further comprising
   generating a modulation wave having a predetermined periodicity providing a first period of stimulation of the perivascular system and a second period of relaxation of the perivascular system, the predetermined periodicity selected to increase waste clearance over continuous stimulation of the perivascular system by the carrier frequency; and
   modulating the carrier wave.

* * * * *